United States Patent
Guo et al.

(10) Patent No.: US 7,666,609 B1
(45) Date of Patent: Feb. 23, 2010

(54) METHOD AND COMPOSITION FOR DIAGNOSIS OF MELANOCYTIC LESIONS

(75) Inventors: Yajun Guo, Omaha, NE (US); Jing Ma, Omaha, NE (US)

(73) Assignee: Shanghai CP GuoJian Pharmaceutical Co. Ltd., Shanghai (CN)

( * ) Notice: Subject to any disclaimer, the term of this patent is extended or adjusted under 35 U.S.C. 154(b) by 161 days.

(21) Appl. No.: 09/915,746

(22) Filed: Jul. 26, 2001

Related U.S. Application Data (63) Continuation of application No. 09/451,353, filed on Dec. 1, 1999, now abandoned.

(60) Provisional application No. 60/110,516, filed on Dec. 1, 1998.

(51) Int. Cl.
 *G01N 33/53* (2006.01)
 *G01N 33/574* (2006.01)

(52) U.S. Cl. .................. 435/7.2; 435/7.23; 435/63; 435/64

(58) Field of Classification Search .............. 530/387.1, 530/388.1, 388.8, 350, 387.7, 387.3; 435/7.1, 435/7.23, 7.72, 40.52; 436/503, 504, 536, 436/64; 424/1.49, 9.6
See application file for complete search history.

(56) References Cited

U.S. PATENT DOCUMENTS

| | | | |
|---|---|---|---|
| 4,036,945 A | 7/1977 | Haber | 424/1 |
| 4,311,688 A | 1/1982 | Burchiel et al. | 424/1 |
| 4,472,371 A | 9/1984 | Burchiel et al. | 424/1.1 |
| 4,478,815 A | 10/1984 | Burchiel et al. | 424/1.1 |
| 4,478,818 A | 10/1984 | Shell et al. | 424/14 |
| RE32,417 E | 5/1987 | Burchiel et al. | 424/1.1 |
| 4,732,864 A | 3/1988 | Tolman | 436/547 |
| 5,223,409 A | 6/1993 | Ladner et al. | 435/69.7 |
| 5,317,091 A | 5/1994 | Subramanian | 424/1.53 |
| 5,475,096 A | 12/1995 | Gold et al. | 536/23.1 |
| 5,530,101 A | 6/1996 | Queen et al. | 530/387.3 |
| 5,595,877 A | 1/1997 | Gold et al. | 435/6 |
| 5,660,985 A | 8/1997 | Pieken et al. | 435/6 |
| 5,693,762 A | 12/1997 | Queen et al. | 530/387.3 |

FOREIGN PATENT DOCUMENTS

| | | |
|---|---|---|
| WO | WO 97/47271 | 12/1997 |
| WO | WO 98/04282 | 2/1998 |
| WO | WO 98/16238 | 4/1998 |
| WO | WO 98/24884 | 6/1998 |

OTHER PUBLICATIONS

The abstract of Chen et al (Journal of Molecular Medicine, May 1998, Vol. 76, p. B11).*
Wilson et al, Biochem Biophys Research Commun, 1981, Vol. 101, pp. 1047-1051 (abstract).*
McCarthy et al, Biochemistry, 1988, Vol. 27, pp. 1380-1388), (abstract).*
The abstract of Sekiguchi et al (Seikagaku, 1989, 61, pp. 89-93).*
Natali et al (British Journal of Cancer, 1995, vol. 71, pp. 1243-1247).*
Trefzer et al, BMC Cancer, 2006, vol. 6, pp. 1-12.*
Kerr and Thorpe (Immunochemistry LabFax, pp. xi, X and 120).*
Aamdal et al. "Immunomagnetie Detection of Melanoma Cells in Bone Marrow and Blood".
Adema et al. "Molecular Characterization of the Melanocyte Lineage-Specific Antigen gp100" J Biol. Chem: 269:20126-20133 (1994).
Argenyi et al. "S100 Protein-Negative Malignant Melanoma: Fact or Fiction? A Light-Microscopic and Immuno-Histochemical Study" Am. J. Dematopathol. 16:233-240 (1994).
Brooks et al. J. "Subtractive Immunization Yields Monoclonal Antibodies that Specifically Inhibit Metastasis" Cell Biol. 122(6):1351-1359 (1993).
Cochran et al. "Detection of S100 Protein as an Aid to the Identification of Melanocytic Tumors" Int. J. Cancer 30:295-297 (1982).
Cohen et al. "Production and Characterisation of an Antimelanoma Mcinoclonal Antibody KBA.62 Using a New Melanoma Cell Line Reactive on Paraffin Wax Embedded Sections" J. Clin. Pathol. 48:826-831 (1995).
Colombari et al. "Distribution of Melanoma Specific Antibody (HMB-45) in Benign and Malignant Melanocytic Tumors" Virchows Archiv. A Pathol Anat. 413:17-24 (1988).
Drier et al. "S100. Protein Immunoreactivity in Poorly Differentiated Carcinomas. Immuno-Histochemical Comparison with Malignant Melanoma" Arch. Pathol. Lab. Med. 111:447-452 (1987).
Emery and Harris. "Strategies for Humanizing Antibodies" Chapter 6 *In Antibody Engineering* $2^{nd}$ Ed. pp. 159-183 (1995).
Esclamado et al. "Unique Proteins Defined by Monoclonal Antibodies Specific for Human Melanoma. Some Potential Clinical Applications" Am. J. Surg. 152:376-385 (1986).

(Continued)

*Primary Examiner*—Karen A Canella
(74) *Attorney, Agent, or Firm*—Fish & Richardson P.C.

(57) ABSTRACT

This invention relates to monoclonal antibodies that recognize an antigen specific to melanocytic lesions. These antibodies are useful in methods of isolating melanoma cells and diagnosing melanocytic lesions. These antibodies are also useful for immunotherapy against melanoma.

5 Claims, 1 Drawing Sheet

OTHER PUBLICATIONS

Frye et al. "Detection of Amplified Oncogenes by Differential Polymerase Chain Reaction" Oncogene 4:1153-1157 (1987).

Gatter et al. "An Immunocytochemical Study. Of Malignant Melanoma and its Differential Diagnosis from Other Malignant Tumors" J. Clin. Pathol. 38:1353-1357 (1985).

Giomo. "A Comparison of Two Immunoperoxidase Staining Methods Based on the Avidin-Biotin Interaction" Diag. Immununol. 2:161-166 (1984).

Gown et al. "Monoclonal Antibodies Spevific for Melanocytic Tumors Distinguished Subpopulations of Melanocytes" Am. J. Pathol. 123:195-203. (1986).

Guo et al. "Inhibition of Human Melanoma Growth and Metstasis In Vivo by Anti-CD44 Monoclonal Antibody" Cancer Res. 54:1561-1565 (1994).

Hachisuka et al. "Immuno-Histochemical Study of S100. Protein and Neuron Specific Enolase )NSE) in Melanocytes and the Related Tumors" Acta Histochem. 80:215-223 (1986).

Harlow and Lane. "Immunoaffinity Purification" Chapter 13 *In Antibodies- A Laboratory Manual* cold Spring Harbor Laboratory pp. 511-552 (1988).

Harlow and Lane. Chapter 12 & 14 *In Antibodies- A Laboratory Manual* Cold .Spring Harbor Laboratory pp. 471-510 & 553-612 (1988).

Herrera and Hancock. "Specificity of Antibody HMB-45" Arch. Pathol. La. Med. 116:900-901 (1992).

Irie et al. "Regression of Cutaneous Metastatic Melanoma by Intralesional Injection with Human Monoclonal Antibody to Ganglioside GD2" Proc..Natl. Acad. Sci. USA 83:8694-8698 (1986).

Kindblom et al. "S100 Protein in Melanocytic Tumors. An Inununo-Histochemical Investigation of Benign and Malignant Melanocytic Tumors and Metastases of Malignant Melanoma and a Characterization of the Antigen in Comparison to Human Brain" Acta. Pathol. Microbiol. Imrnunol. Scand. 92:219-230 (1984).

Köhler et al. "Derivation of Specific Antibody. Producing Tissue Culture and Tumor Lines by Cell Fusion" Eur. J. Immunol. 6:511-519 (1976).

Mackie et al. "Use of NK1 C3 Monoclonal Antibody in the Assessment of Benign and Malignant Melanocytic Lesions" J. Clin. Pathol. 37:367-372 (1984) .

Mottolese et al. "Immunocytochemical Diagnosis of Amelanotic Metastatic Melanoma Using Monoclonal Antibodies HMB-45 and Ep1-3" Melanoma Res. 4:53-58 (1994).

Nakajima et al. "Immuno-Histochemical Demonstration of S100 Protein in Malignant Melanoma and Pigmented Nevus and its Diagnostic Application" Cancer 50:912-918 (1982).

Ordonez et al. "Comparison of HMB-45 Monoclonal Antibody and S100 Protein in the Immuno-Histochemical Diagnosis of Melanoma" Am. J. Clin. Pathol. 90:385-390 (1988).

Palazzo and Duray. "Typical, Dysplastic, Congenital, and Spitz Nevi: A Comparative Immuno-Histochemical Study" Hum. Pathol. 20:341-346 (1989).

Rothman et al. "Structure and Expression of Germ Line Immunoglobulin Heavy-Chain ε Transcripts: Interleukin-4 Plus Lipopolysaccharide-Directed Switching to Cε" Molecular and Cellular Biology 10(4):1672-1679 (1990).

Serafini et al. "Technetium —99m Labeled Monoclonal Antibodies in the Detection of Metastatic Melanoma" Clinical Nuclear Medicine 14(8):580-587 (1989).

Shi et al. "Antigen Retrieval in Formalin-Fixed, Paraffin-Embedded Tissues: An Enhancement Method for Immuno-Histochemical Staining Based on Microwave Oven Heating of Tissue Sections" J. Histochem Cytochem. 39:741-748 (1991).

Smoller et al. "HMB-45 Staining of Dysplastic Nevi. Support for a Spectrum of Progression Toward Melanoma" A. J. Surg. Pathol. 13:680-684 (1989).

Smoller. "Immunohistochemistry in the Diagnosis of Melanocytic Neoplasms" Pathology: State of the Art Reviews 2:371-383 (1994).

Springall et al. "The Value of S100 Immunostaining as a Diagnostic Tool in Human Malignant Melanomas. A Comparative Study Using S100 and Neuron-Specific Enolase Antibodies" Virchows Arch. Pathol. Anat. Histopathol. 400:331-343 (1983).

Stefansson et al. "Distribution of S100 Protein Outside the Central Nervous System" Brain Res. 234:309-317 (1982).

Stefansson et al. "S100 Protein in Human Chondrocytes" Nature 295:63-64 (1982).

Sun et al. "Antibody HMB-45 Identifies the Cells of Blue Nevi. An Immuno-Histochemical Study on Paraffin Sections" Am. J. Surg. Pathol. 14:748-751 (1990).

Swerdlow et al. "Risks of Second Primary Malignancy in Patients with Cutaneous and Ocular Melanoma in Denmark, 1943-1989" Int. J. Cancer 61:773-779 (1995).

Tabuchi et al. "A S100 Protein in Human Glial Tumors. Qualitative and Quantitative Studies" Aca Neurochir. Wien 65:239-251(1982).

Trefzer et al. "SM5-1: A New Monoclonal Antibody Which is Highly Sensitive and Specific for Melanocytic Tumors" Journal of Dermatological Science 16(Suppl. 1):S110 (1998).

Vanstapel et al. "New Sites of Human S100 Immunoreactivity Detected with Monoclonal Antibodies" Am. J. Clin. Pathol. 85:160-168 (1986).

Vennegoor et al. "Biochemical Characterization and Cellular Localization of a Formalin-Resistant Melanoma-Associated Antigen Reacting with Monoclonal Antibody NKI/C-3" Int. J. Cancer 35:287-295 (1985).

Wick et al. "Recognition of Malignant Melanoma by Monoclonal Antibody HMB-45. An Immuno-Histochemical Study of 200 Paraffin-Embedded Cutaneous Tumors" J. Cutan. Pathol. 15:201-207 (1988).

Williams et al "Subtractive Immunization Techniques for the Production of Monoclonal Antibodies to Rare Antigens" Biotechniques 12:842-847 (1992).

Trefzer at al., *The monoclonal antibody SM5-1 recognizes a fibronectin variant which Is widely expressed in melanoma*, BMC Cancer, Jan. 11, 2006, vol. 6 (No. 8) pp. 1-12.

Trefzer et al., Arch. Dermatol. Res. (2000) 292:583-589.

Trefzer et al., Arch. Dermatol. Res. (2000) 292:583-589.

Trefzer et al., BMC Cancer (2006) 6(8):1-12.

* cited by examiner

FIG. 1

METHOD AND COMPOSITION FOR DIAGNOSIS OF MELANOCYTIC LESIONS

This application is a continuation of application Ser. No. 09/451,353, filed Dec. 1, 1999, entitled: METHODS AND COMPOSITION FOR DIAGNOSIS OF MELANOCYTIC LESIONS, now abandoned.

I. FIELD OF THE INVENTION

This invention relates to melanoma-associated antigens, antibodies against melanoma-associated antigens, and diagnostic and therapeutic methods concerning melanoma.

II. BACKGROUND OF THE INVENTION

Human malignant melanoma usually starts as harmless moles that undergo radial to invasive growth and end in the destructive stage of metastatic melanoma. Melanoma usually resists chemotherapy and radiotherapy. Surgery is the most effective treatment. Early diagnosis is required for surgery to be effective, which is unfortunately hampered by the lack of markers that are sensitive and specific for melanoma.

The commonly used antibodies for immuno-histochemical diagnosis of melanoma are HMB-45, anti-S-100 and NKI/C3 (for a review, please see Smoller B R, "Immunohistochemistry in the Diagnosis of Melanocytic Neoplasms", in *PATHOLOGY: State of the Art Reviews,* 2:371–383, 1994).

HMB-45 has been shown to react with the melanoma-associated antigen gp-100. Adema G J, de-Boer A J, Vogel A M, Loenen W A, Figdor C G: Molecular characterization of the melanocyte lineage-specific antigen gp 100. *J. Biol. Chem.* 1994; 269:20126–20133. HMB-45 reacts with melanoma, junctional nevi, dysplastic nevi, spindle cell and epitheloid cell nevi, congenital nevi and blue nevi. Gown A M, Vogel A M, Hoak D, Gough F, McNutt M A: Monoclonal antibodies specific for melanocytic tumors distinguish subpopulations of melanocytes. *Am. J. Pathol.* 1986; 123:195–203; Esclamado R M, Gown A M, Vogel A M. Unique proteins defined by monoclonal antibodies specific for human melanoma. Some potential clinical applications. *Am. J. Surg.* 1986; 152:376–385; Palazzo J, Duray P H: Typical, dysplastic, congenital, and Spitz nevi: a comparative immuno-histochemical study. *Hum Pathol* 1989; 20:341–346; Smoller B R, McNutt N S, Hsu A: HMB-45 recognizes stimulated melanocytes. *J. Cutan. Pathol.* 1989; 16:49–53; Smoller B R, McNutt N S, Hsu A: HMB-45 staining of dysplastic nevi. Support for a spectrum of progression toward melanoma. *Am J Surg Pathol* 1989; 13:680–684; Sun J, Morton T H Jr., Gown A M: Antibody HMB-45 identifies the cells of blue nevi. An immuno-histochemical study on paraffin sections. *Am J Surg Pathol* 1990; 14:748–751. HMB-45 is routinely used as a marker to differentiate melanoma from nonmelanocytic cancer cells. Herrera G A, Hancock C. Specificity of antibody HMB-45. *Arch. Pathol. La. Med.* 1992; 116:900–901. However, diagnosis with HMB-45 leaves a sizable numbers of melanomas undetected because the sensitivity of HMB-45 is between 67% and 93%. Wick M R, Swanson P E, Rocamora A. Recognition of malignant melanoma by monoclonal antibody HMB-45. An immuno-histochemical study of 200 paraffin-embedded cutaneous tumors. *J Cutan Pathol* 1988; 15:201–207; Ordonez N G, Ji X L, Hickey R C: Comparison of HMB-45 monoclonal antibody and S100 protein in the immuno-histochemical diagnosis of melanoma. *Am. J. Clin. Pathol.* 1988; 90:385–390.

Antibodies to S-100 protein have higher sensitivity than HMB-45 with malignant melanoma varieties. Nakajima T, Watanabe S, Sato Y, Kameya T, Shimosato Y, Ishihara K: Immuno-histochemical demonstration of S100 protein in malignant melanoma and pigmented nevus and its diagnostic application. *Cancer* 1982; 50:912–918; Kindblom L G, Lodding P, Rosengren L, Baudier J, Haglid K: S100 protein in melanocytic tumors. An immuno-histochemical investigation of benign and malignant melanocytic tumors and metastases of malignant melanoma and a characterization of the antigen in comparison to human brain. *Acta. Pathol. Microbiol Immunol. Scand.* 1984; 92:219–230; Springall D R, Gu J, Cocchia D, Michetti F, Levene A, Levene M M et al: The value of S100 immunostaining as a diagnostic tool in human malignant melanomas. A comparative study using S100 and neuron-specific enolase antibodies. *Virchows Arch. Pathol. Anat. Histopathol.* 1983; 400:331–343; Cochran A J, Wen D R, Herschman H R, Gaynor R B: Detection of S100 protein as an aid to the identification of melanocytic tumors. *Int. J. Cancer* 1982; 30:295–297; Gatter K C, Ralfkiaer E, Skinner J, Brown D, Heryet A, Pulford K A et al: An immunocytochemical study of malignant melanoma and its differential diagnosis from other malignant tumors. *J Clin Pathol* 1985; 38:1353–1357; Hachisuka H, Sakamoto F, Nomura H, Mori O, Sasai Y: Immuno-histochemical study of S100 protein and neuron specific enolase (NSE) in melanocytes and the related tumors. *Acta Histochem.* 1986; 80:215–223; Argenyi Z B, Cain C, Bromley C, Nguyen A V, Abraham A A, Kerschmann R et al: S100 protein-negative malignant melanoma: fact or fiction? A light-microscopic and immuno-histochemical study. *Am. J. Dermatopathol.* 1994; 16:233–240 (11–17). However, anti-S100 antibodies are notoriously unspecific. Anti-S100 antibodies have been shown to stain benign cells such as salivary and sweat glands, skeletal and cardiac muscle, histiocytes, Schwann cells, lipocytes, chondrocytes, astrocytes, oligodendrocytes (Kindblom L G, Lodding P, Rosengren L, Baudier J, Haglid K: S100 protein in melanocytic tumors. An immuno-histochemical investigation of benign and malignant melanocytic tumors and metastases of malignant melanoma and a characterization of the antigen in comparison to human brain. *Acta. Pathol. Microbiol Immunol. Scand.* 1984; 92:219–230; Stefansson K, Wollmann R L, Moore B W, Arnason B G. S100 protein in human chondrocytes. *Nature* 1982; 295:63–64; Stefansson K, Wollmann R L, Moore B W: Distribution of S100 protein outside the central nervous system. *Brain Res.* 1982; 234:309–317) and tumors arising from these cells (Tabuchi K, Moriya Y, Furuta T, Ohnishi R, Nishimoto: A S100 protein in human glial tumors. Qualitative and quantitative studies. *Acta Neurochir Wien* 1982; 65:239–251; Vanstapel M J, Gatter K C, de Wolf Peeters C, Mason D Y, Desmet V D. New sites of human S100 immunoreactivity detected with monoclonal antibodies. *Am J Clin Pathol* 1986; 85:160–168). Anti-S100 antibodies have also been shown to stain many non-melanoma malignant tumor tissues. Drier J K, Swanson P E, Cherwitz D L, Wick M R: S100 protein immunoreactivity in poorly differentiated carcinomas. Immuno-histochemical comparison with malignant melanoma. *Arch. Pathol. Lab. Med.* 1987; 111:447–452.

NKI/C3 antibody also reacts with a broad range of benign and malignant neoplasms. Mackie R M, Campbell I, Turbitt M L. Use of NK1 C3 monoclonal antibody in the assessment of benign and malignant melanocytic lesions. *J Clin Pathol* 1984; 37:367–372; Vennegoor C, Calafat J, Hageman P, van Buitenen F, Janssen H, Kolk A et al. Biochemical characterization and cellular localization of a formalin-resistant melanoma-associated antigen reacting with monoclonal antibody NKI/C-3. *Int. J. Cancer* 1985; 35:287–295. These unspecific activities limit the usefulness of NKI/C3 antibody in the diagnosis of melanocytic lesions.

KBA.62 antibody is comparable to HMB-45 in its sensitivity to melanoma, but is less specific than HMB-45 in that KBA.62 stains squamous cell carcinoma and basal cell carcinomas. Cohen Knafo E, al Saati T, Aziza J, Ralfkiaer E, Selves J, Gorguet B et al: Production and characterisation of an antimelanoma monoclonal antibody KBA.62 using a new melanoma cell line reactive on paraffin wax embedded sections. *J Clin Pathol* 1995; 48:826–831.

III. SUMMARY OF THE INVENTION

Within the scope of this invention, Applicant prepared a melanoma specific monoclonal antibody, SM5-1, using a subtractive immunization protocol. Immuno-histochemical staining of paraffin-embedded specimens of melanomas (primary melanomas and metastases) and skin nevi samples showed that SM5-1 reacts with all nevi and malignant melanocytic lesions. On the other hand, SM5-1 does not react with non-activated epidermal melanocytes, non-melanocytic tumor cells listed in Table 2, keratinocytes, endothelial cells, smooth muscle cells and peripheral nerves. These results indicate that SM5-1 is extremely sensitive and highly specific for melanocytic lesions.

A hybridoma secreting SM5-1 antibody was deposited with American Type Culture Collection, at 10801 University Boulevard, Manassas, Va., 20110–2209, U.S.A., on Oct. 20, 1998 under ATCC Accession No. HB-12588.

A. Antigen

Thus, in one aspect, this invention features an isolated, purified, enriched, or synthetic antigen which binds specifically to SM5-1 antibody. In addition, this antigen is characterized in that it is present on the membrane and in the cytoplasm of all human melanoma cells, including human nevi, primary melanoma cells, and metastatic melanoma cells. Furthermore, this antigen is characterized in that it is not detectably expressed in normal non-activated human melanocytic cells as tested by SM5-1 antibody. Neither is this antigen detectably expressed in human tumor cells listed in Table 2 as tested by SM5-1 antibody. This antigen may be obtained from natural sources (e.g., cells or extracellular fluid) or by chemical synthesis.

The antigen of this invention can be used to prepare a melanoma vaccine to elicit a specific immunological response against melanoma for treating or preventing the development or spread of melanoma. For this purpose, the melanoma antigen can be mixed with an adjuvant (an agent which increases the immune response for the immunization procedure), including, but not limited to, Freund's complete adjuvant (emulsion of mineral oil, water, and mycobacterial extracts), Freund's incomplete adjuvant (emulsion of water and oil only), mineral gels, e.g. aluminum hydroxide gels, surface active substances such as lysolecithin, polyanions, peptides, BCG (Bacillus Calmette-Guerin). The routes of immunization include, among others, intradermal, subcutaneous, intramuscular, intraperitoneal, intraspleen, intralymphnode, intratumor, intravascular and intracranial injections. A series of injections can be given to achieve high antibody titers and/or T cell response. For example, the immunization is performed by injecting the antigen two, three, four or more times parenterally, e.g. intraperitoneally and/or subcutaneously, in regular or irregular intervals of a few days, e.g. three to seven days, up to several months, for example four weeks.

By "isolated" in reference to a polypeptide (e.g., an antigen or an antibody) is meant a polypeptide that is isolated from a natural source (e.g., cells, including tumor cells, or extracellular fluid) or that is synthesized. The isolated polypeptides of the present invention are unique in the sense that they are not found in a pure or separated state in nature. Use of the term "isolated" indicates that a naturally occurring sequence has been removed from its normal cellular environment. Thus, the polypeptide may be in a cell-free solution or placed in a different cellular environment. The term does not imply that the polypeptide is the only amino acid chain present, but that it is the predominate amino acid chain present (at least 10–20% more than any other sequence) and is essentially free (about 90–95% pure at least) of non-amino acid material naturally associated with it.

By "enriched" in reference to a polypeptide (e.g., an antigen or an antibody) is meant that the specific polypeptide constitutes a significantly higher fraction (2–5 fold) of the total of amino acid chains present in the cells or solution of interest than in normal or diseased cells or in the cells from which the sequence was taken. This could be caused by a person by preferential reduction in the amount of other amino acid chains present, or by a preferential increase in the amount of the specific polypeptide of interest, or by a combination of the two. However, it should be noted that enriched does not imply that there are no other amino acid sequences present, just that the relative amount of the polypeptide of interest has been significantly increased. The term "significantly" here is used to indicate that the level of increase is useful to the person making such an increase, and generally means an increase relative to other amino acid chains of about at least 2 fold, more preferably at least 5 to 10 fold or even more. The term also does not imply that there is no amino acid chains from other sources.

By "purified" in reference to a polypeptide (e.g., an antigen or an antibody) does not require absolute purity (such as a homogeneous preparation); instead, it represents an indication that the polypeptide is relatively purer than in the natural environment (compared to the natural level this level should be at least 2–5 fold greater, e.g., in terms of mg/ml). Purification of at least one order of magnitude, preferably two or three orders, and more preferably four or five orders of magnitude is expressly contemplated. The substance is preferably free of contamination at a functionally significant level, for example 90%, 95%, or 99% pure.

B. Antibody and Other Affinity Molecules

In a second aspect, the present invention features an affinity molecule that recognizes the antigen recognized by the SM5-1 antibody. Affinity molecules include, but are not limited to, antibody, peptide, nucleic acid aptamer, and other organic polymers with specific binding affinity to the antigen. In a preferred embodiment, the affinity molecule is a monoclonal antibody. Different monoclonal antibodies of this invention may recognize different epitopes on the antigen. Preferably, the monoclonal antibody of this invention is purified, isolated or enriched.

In a preferred embodiment, this monoclonal antibody (i) recognizes an antigen on the membrane and in the cytoplasm of human nevi, primary melanoma cells, and metastatic melanoma cells, (ii) does not recognize an antigen on normal non-activated human melanocytes, and (iii) does not recognize an antigen on human tumor cells listed in Table 2.

In another preferred embodiment, the present invention contemplates monoclonal antibodies that correspond to the monoclonal antibody produced by ATCC HB-12588, and, in a particularly preferred embodiment, the ATCC HB-12588 antibody. One antibody corresponds to another antibody if they both recognize the same or overlapping antigen binding sites as demonstrated by, for example, a binding inhibition assay.

The antibodies obtained and employed may be any one of the immunoglobulin classes, such as IgA, IgD, IgE, IgG and IgM, and any one of the subclasses of the various classes. In addition, whole antibodies or fragments of the antibodies may be employed, such as FAB, F(ab)'$_2$, Fv, or the like. The subject immortalized B-lymphocytes or other cells, for example T-cells, which provide monoclonal antibodies specific for the subject epitope, can be used as a source of DNA, either genomic or cDNA, for expression of the ligand heavy chains of the monoclonal antibodies in procaryotes or eucaryotes. The resulting products may then be used as receptors for binding to the subject epitopes.

The present invention also provides derivatives of antibodies that possess the same binding specificity as the antibodies of the invention as described above. These derivatives contain modifications in a region that is not important for antigen binding. These antibody derivatives can be obtained from antibodies according to the present invention by exchanging one or more constant domains and/or linkages with another molecule. Thus, for example, an exchange of constant domains can be carried out where, for example, an antibody of class IgM can be converted into an antibody of class IgG with maintenance of its antigen specificity. This and other isotype switches can be carried out by cell-biological or molecular-biological methods known to those skilled in the art, including, but are not limited to, that described in Rothman et al., (1990) *Mol. Cell. Biol.,* 10:1672–1679. In another example, the constant domains of a murine antibody of this invention can be exchanged for the constant domains of a human antibody. Methods of preparing humanized antibody are applicable to the present invention, including, but not limited to, those methods described and cited in U.S. Pat. Nos. 5,530,101 and 5,693,762, both entitled "Humanized immunoglobulins", and WO 98/24884 entitled "Transgenic non-human animals capable of producing heterologous antibodies", both of which are incorporated by reference herein.

The monoclonal antibodies of the present invention can also be linked with another molecule, especially a label or a toxin, including, but not limited to, enzymes such as peroxidase, toxins such as ricin or cholera toxin, and fluorescent and radioactive labels.

Monoclonal antibodies can be produced readily by one skilled in the art using cell fusion techniques. Immortal, antibody-secreting cell lines can also be produced by techniques other than fusion, such as direct transformation of B-lymphocytes with oncogenic DNA, virus or other means. Different antigen sources can be used to challenge the normal B-lymphocyte population that is later converted to an immortal cell line. For example, the antigen immunoprecipitated by SM5-1 antibody can be used as an immunogen to challenge the mammal (e.g., mouse, rat, hamster, etc.) used as a source for normal B-lymphocytes. The antigen-stimulated B-lymphocytes are then harvested and fused to an immortal cell line or transformed into an immortal cell line by any appropriate technique. Antibody-producing immortal cells can be screened for anti-melanoma cell antibody production by selecting clones that are strongly reactive with the antigen or by selecting clones that compete with SM5-1 for reaction with melanoma cells and/or the isolated or purified antigen.

Other than monoclonal antibodies, this invention also features peptides, nucleic acid aptamers and other molecules that recognize the antigen recognized by the SM5-1 antibody. Methods of selecting affinity peptides and aptamers are applicable to the present invention, including, but not limited to, those methods described and cited in U.S. Pat. Nos. 5,223,409, 5,475,096, 5,595,877, and 5,660,985, all of which are incorporated by reference herein.

C. Hybridoma Cell Lines

In a third aspect, the present invention features a continuous cell line that produces an above-described antibody of the present invention. In a preferred embodiment, this cell line is a hybridoma. In another preferred embodiment, this cell line is an immortal cell line.

D. Isolating Melanoma Cells and Other Cells Expressing the Antigen Recognized by SM5-1

The monoclonal antibodies and other affinity molecules of the present invention facilitate the isolation of melanoma antigen. One can use techniques described in Chapter 13 of Harlow and Lane, "Immunoaffinity Purification", pages 511–552, ANTIBODIES—A LABORATORY MANUAL, Cold Spring Harbor Laboratory, 1988, incorporated by reference herein.

The monoclonal antibodies and other affinity molecules of the present invention facilitate the isolation of melanoma cells. Thus, in a fourth aspect, the present invention provides a method of producing a population of human cells enriched with human melanoma cells comprising: (a) providing a cell suspension from human tissue suspected of containing melanoma cells; (b) contacting said cell suspension with a monoclonal antibody (or another affinity molecule) that recognizes the antigen recognized by the SM5-1 antibody; and (c) separating and recovering from said cell suspension the cells bound by said antibody.

Human melanoma cells and other cells that express the antigen recognized by SM5-1 can be separated from other cells with the antibodies of this invention using the indirect immune adherence ("panning") techniques and the fluorescence-activated cell sorting (FACS) techniques and other techniques known to those skilled in the art. For example, the antibody bound to the cell can be labeled and then the cells separated by a mechanical cell sorter that detects the presence of the label. Fluorescence-activated cell sorters are well known in the art.

In another example, the anti-melanoma antibody or another affinity molecule is attached to a solid support. Various solid supports are known to those skilled in the art, including, but not limited to, agarose beads, magnetic beads, polystyrene beads, hollow fiber membranes and plastic petri dishes. Cells that are bound by the antibody can be removed from the cell suspension by simply physically separating the solid support from the cell suspension.

Thus, in a fifth aspect, the present invention features isolated, purified or enriched human melanoma cells, e.g., a suspension of human cells comprising human melanoma cells substantially free of normal human melanoma cells and non-melanocytic tumor cells. The isolated melanoma cells or other cells expressing the antigen recognized by SM5-1 can be employed to produce anti-tumor antibodies, cytotoxic T cells and cellular vaccines against melanoma using techniques known to those skilled in the art, including, but not limited to, those described and cited in PCT publications WO 97/47271, WO 98/16238 and WO 98/04282, all of which are incorporated by reference herein.

E. Immuno-Histochemistry Diagnosis

The monoclonal antibodies and other affinity molecules of this invention can be used to screen patient samples for melanoma, including tissue biopsy specimens, blood and other body fluid samples.

Biopsy specimens can be used for diagnosis of melanoma with immunohistochemical staining techniques. The tissue sample may be fixed in formalin or other standard histological preservatives, dehydrated and embedded in paraffin as is routine in hospital pathology laboratory. Sections can be cut from the paraffin embedded material and mounted on glass slides or the sections can be prepared from cryo-preserved tissue. Alternatively, cytological preparations can be used. For example, cells from the tissue sample can be fixed on a slide, typically by exposure to formalin in a buffer at physiologic pH, followed by suspension in acetone and pelleting onto gelatin-coated slides by centrifugation. The cellular antigen can be localized, either by exposure to labeled antibody or by exposure to unlabeled antibody and a labeled secondary antibody. The amount of the cell surface protein or antigen in the sample is proportional to the amount of bound label. In a preferred embodiment, SM5-1 is used in the immuno-histochemical evaluation of melanoma.

F. Serum Diagnosis

Aside from biopsy specimens, the melanoma antigen defined by the monoclonal antibodies of this invention can be detected in tissue samples and bodily fluids by immunological methods known to those skilled in the art. Sample preparation will vary depending on the source of the biological sample. Tissue samples may be prepared by lysing the cells. Serum samples can be prepared by clotting whole blood and isolating the supernatant in accordance with well-known methods. Urine, bile fluid and other body fluid samples may be concentrated before testing. A wide variety of techniques and protocols exist for detecting an antigen in a sample suspected of containing the antigen. One can use techniques described in Chapters 12 and 14 of Harlow and Lane, "Immunoblotting" and "Immunoassays", pages 471–510 and 552–612, respectively, ANTIBODIES—A LABORATORY MANUAL, Cold Spring Harbor Laboratory, 1988, incorporated by reference herein.

For example, two or more monoclonal antibodies can be used and the incubation with the individual antibodies can take place in various sequences in homogeneous or heterogeneous phase. A signal is generated due to binding of at least two monoclonal antibodies with the antigen to be detected in the body fluid sample. The determination can take place either in homogeneous phase (e.g., agglutination test). The determination can also take place in heterogeneous phase (e.g., sandwich immunoassay). In both cases, at least two monoclonal antibodies are used which bind to non-overlapping epitopes on the antigen.

A wide variety of labels can be used, such as radio-nuclids, enzymes, fluorescers, fluorescer-quencher combinations, chemiluminescers, magnetic particles, radiopaque dyes, and the like. These labels can be directly conjugated to the monoclonal antibody through a variety of covalently bonded linking groups and functionalities. Some of the techniques involve having one of the members of the antigen-antibody complex bound to a support, such as a particle or vessel wall. Other assays are performed in solution without a separation step, where uncomplexed label is separated from complexed label. In a number of assays, the antibody need not be labeled, such as in hemagglutination or where anti-immunoglobulin is employed and the anti-immunoglobulin is labeled, so as to provide for indirect labeling of the subject monoclonal antibody. Applicable assays include ELISA, RIA, EIA (Frye, et al., (1987) *Oncogene* 4:1153–1157) and the like.

The invention also concerns test kits for the qualitative and quantitative determination of the melanoma-associated antigen comprising monoclonal antibodies or other affinity molecules of the invention and/or derivatives thereof and, optionally, other polyclonal or monoclonal antibodies and/or adjuncts.

Test kits according to the invention for a radioimmunoassay contain, for example, a suitable carrier, optionally freeze-dried solutions of one or more polyclonal and/or monoclonal antibodies, solutions of a radioactively labeled antibody, standard solutions of the melanoma antigen, buffer solutions, and, optionally, polypeptides or detergents for preventing non-specific adsorption and aggregate formation, pipettes, reaction vessels, calibration curves, instruction manuals and the like. One of the antibodies of the test kit is a monoclonal antibody against the melanoma antigen.

Test kits according to the invention for an enzyme immunoassay contain, for example, a suitable carrier, optionally freeze-dried solutions of one or more polyclonal and/or monoclonal antibodies, optionally freeze-dried or concentrated solutions of an enzyme- or biotin-conjugated antibody, solutions of an enzyme-avidin conjugate if biotin-labeled antibody is used, enzyme substrate in solid or dissolved form, standard solutions of the melanoma antigen, buffer solutions, and, optionally, polypeptides or detergents for preventing non-specific adsorption and aggregate formation, pipettes, reaction vessels, calibration curves, instruction manuals and the like. One of the antibodies of the test kit is a monoclonal antibody against the melanoma antigen.

The invention also concerns test kits for the qualitative and quantitative determination of the melanoma-associated antigen comprising monoclonal antibodies of the invention and/or derivatives thereof and, optionally, other polyclonal or monoclonal antibodies and/or adjuncts.

Test kits according to the invention for a radioimmunoassay contain, for example, a suitable carrier, optionally freeze-dried solutions of one or more polyclonal and/or monoclonal antibodies, solutions of a radioactively labeled antibody, standard solutions of the melanoma antigen, buffer solutions, and, optionally, polypeptides or detergents for preventing non-specific adsorption and aggregate formation, pipettes, reaction vessels, calibration curves, instruction manuals and the like. One of the antibodies of the test kit is a monoclonal antibody against the melanoma antigen.

Test kits according to the invention for an enzyme immunoassay contain, for example, a suitable carrier, optionally freeze-dried solutions of one or more polyclonal and/or monoclonal antibodies, optionally freeze-dried or concentrated solutions of an enzyme- or biotin-conjugated antibody, solutions of an enzyme-avidin conjugate if biotin-labeled antibody is used, enzyme substrate in solid or dissolved form, standard solutions of the melanoma antigen, buffer solutions, and, optionally, polypeptides or detergents for preventing non-specific adsorption and aggregate formation, pipettes, reaction vessels, calibration curves, instruction manuals and the like. One of the antibodies of the test kit is a monoclonal antibody against the melanoma antigen.

G. Monitoring Melanoma Therapy

The antibodies and other affinity molecules of the present invention can also be used for the determination of a prognostic index that indicates the level of melanoma antigen in the body fluids (esp. serum) before, during and following a treatment such as surgery, chemotherapy or radiation therapy. Recurrences of the tumor could be detected by running tests on fluids for the antigen.

H. Whole Body or Local Imaging

Whole body and local imaging techniques employing radioisotope labels can be used for locating melanomas, both primary tumors and tumors which have metastasized. The antibodies and other affinity molecules of the present invention are bound to a suitable radioisotope, typically technetium-99, $^{123}$I, $^{125}$I, or $^{131}$I, or a combination thereof, and administered to a patient (e.g., parentally). High specific activity labeling of antibodies or fragments with technetium-99m is described for example in U.S. Pat. Nos. 5,317,091, 4,478,815, 4,478,818, 4,472,371, Re. 32,417, and 4,311,688. The bio-distribution of the label is monitored by scintigraphy, and accumulations of the label are related to the presence of melanoma cells. Whole body imaging techniques are described in U.S. Pat. Nos. 4,036,945 and 4,311,688. Other examples of agents useful for diagnosis and therapeutic use which can be coupled to antibodies and antibody fragments include metallothionein and fragments (see, U.S. Pat. No. 4,732,864). The disclosures of the cited patents are incorporated herein by reference.

I. Therapeutic Methods

The monoclonal antibodies and other affinity molecules of the present invention can be used for combating melanoma cells especially for the passive immunization of melanoma patients. Thus, the present invention also provides a pharmaceutical composition comprising one or more antibodies or other affinity molecules of the present invention, optionally together with conventional pharmaceutical carrier, adjuvant, filling and additive materials. The pharmaceutical composition can be administered to melanoma patients.

In a preferred embodiment, the unit dosage of the antibody according to the present invention for passive immunization is in the range of from about 1 to about 200 mg. The unit dosage can be repeatedly administered to melanoma patients. The monoclonal antibodies can be administered locally into the melanoma, see Irie et al., (1986) Proc. Natl. Acad. Sci. USA, 83:8694–8698, or administered systemically into the patient (especially after metastasis). The antibodies according to the present invention can be used therapeutically alone or as conjugates with toxins, radioactive agents, and other therapeutics.

The melanoma antigen can be coated on antigen presenting cells (APC) or be transfected or pulsed into antigen presenting cells (including, but not limited to, dentritic cells, B cells, and macrophages) to prepare cellular vaccines that can stimulate immune response against melanoma cells for treating or preventing melanoma. The isolated melanoma cells can be fused with antigen presenting cells to prepare cellular vaccines that can stimulate immune response against melanoma cells for treating or preventing melanoma. The above-described cellular vaccines can be augmented by cytokine treatment and/or attaching a bridge molecule (such as a bispecific monoclonal antibody) that binds to a costimulatory molecule (e.g., CD28 or 4-1BB) on T cells using techniques described and cited in PCT publications WO 97/47271, WO 98/16238 and WO 98/04282.

J. Monitoring the Level of Antibodies Against the Melanoma Antigen

The antibodies to the melanoma antigen may themselves be used as antigens for the production of antibodies specific for the idiotypic side of the monoclonal antibody to the melanoma antigen. The anti-idiotype polyclonal or monoclonal antibody can be used to detect the presence of antibodies in a host to the melanoma antigen, where the antibody to the melanoma antigen and the physiological fluid to be diagnosed are from the same host. For example, where the antibody to the melanoma antigen is a human antibody or a humanized antibody, this antibody can itself be used as an antigen to make a monoclonal antibody specific for the human idiotype. This anti-idiotype monoclonal antibody can be used to detect the level of antibodies to the melanoma antigen in a human physiological fluid, for example blood, serum or urine. The anti-idiotype monoclonal antibody can be made in any host, for example rodent, more particularly rat or mouse. The anti-idiotype monoclonal antibody can also be a humanized or human antibody.

The anti-idiotype monoclonal antibodies can be used as such or in the form of radioactively labeled derivatives in a radioimmunoassay (RIA). Any of the known modifications of a RIA can be used, for example soluble phase homogeneous) RIA, solid phase (heterogeneous) RIA, single RIA or double (sandwich) RIA with direct or indirect (competitive) determination of antibodies directed against melanoma antigen.

In a sandwich RIA, for example, a suitable carrier is coated with an anti-idiotype monoclonal antibody by simple adsorption or optionally after activation of the carrier (such as with glutaraldehyde or cyanogen bromide). Suitable carriers include, but are not limited to, the plastic surface of a microtiter plate or of a test tube (e.g., of polystyrene, polypropylene or polyvinylchloride), glass or plastic beads, filter paper, dextran, cellulose acetate or nitrocellulose sheets, magnetic particles.

Then test solutions containing antibodies directed against the melanoma antigen and finally radioactively labeled polyclonal antibodies which also react with the antibodies directed against the melanoma antigen are added. The amount of antibodies directed against the melanoma antigen in the test solution is directly proportional to the amount of bound polyclonal antibodies and is determined by measuring the radioactivity of the solid phase.

The anti-idiotype monoclonal antibodies can be used as such or in the form of enzyme-conjugated derivatives in an enzyme immunoassay. Any of the known modifications of an enzyme immunoassay can be used. The tests are carried out in an analogous manner to the radioimmunoassays described above using an enzyme label instead of a radioactive label. The amount of immune complex formed which corresponds to the amount of antibodies directed against the melanoma antigen is determined by adding an enzyme substrate solution. The enzyme substrate reaction results, for example, in a color change which can be observed by eye or with optical measuring devices.

The anti-idiotype monoclonal antibodies of the present invention can be used as such or in the form of derivatives conjugated with chemiluminescent markers in a chemiluminescence immunoassay. Any of the known modifications of a chemiluminescence immunoassay can be used. The tests are carried out in an analogous manner to the radioimmunoassays described above using a chemiluminescent label instead of a radioactive label. The amount of immune complex formed which corresponds to the amount of antibodies directed against the melanoma antigen is determined by adding a compound triggering luminescence, e.g. $H_2O_2$ and NaOH, and measuring the emission of light with optical measuring devices.

The anti-idiotype monoclonal antibodies and derivatives thereof as described herein before can also be used with other immunoassays, including, but not limited to, immunofluorescence assays, latex agglutination, hemagglutination, evanescent light assays using an optical fiber coated with an anti-idiotype MAb and other direct-acting immunosensors which convert the binding event into an electrical or optical signal, or the like.

The invention also concerns test kits for the qualitative and quantitative determination of antibodies directed against the melanoma-associated antigen comprising anti-idiotype monoclonal antibodies of the invention and/or derivatives thereof and, optionally, other polyclonal or monoclonal antibodies and/or adjuncts.

Test kits according to the invention for a radioimmunoassay contain, for example, a suitable carrier, optionally freeze-dried solutions of one or more polyclonal and/or monoclonal antibodies, solutions of a radioactively labeled antibody, standard solutions of antibodies directed against the melanoma antigen, buffer solutions, and, optionally, polypeptides or detergents for preventing non-specific adsorption and aggregate formation, pipettes, reaction vessels, calibration curves, instruction manuals and the like. One of the antibodies of the test kit is an anti-idiotype monoclonal antibody.

Test kits according to the invention for an enzyme immunoassay contain, for example, a suitable carrier, optionally freeze-dried solutions of one or more polyclonal and/or monoclonal antibodies, optionally freeze-dried or concentrated solutions of an enzyme- or biotin-conjugated antibody, solutions of an enzyme-avidin conjugate if biotin-labeled antibody is used, enzyme substrate in solid or dissolved form, standard solutions of antibodies directed against the melanoma antigen, buffer solutions, and, optionally, polypeptides or detergents for preventing non-specific adsorption and aggregate formation, pipettes, reaction vessels, calibration curves, instruction manuals and the like. One of the antibodies of the test kit is an anti-idiotype monoclonal antibody.

K. Pharmaceutical Formulations and Modes of Administration

Pharmaceutical compositions suitable for use in the present invention include compositions wherein the active ingredients are contained in an effective amount to achieve its intended purpose. Determination of the effective amounts is well within the capability of those skilled in the art, especially in light of the detailed disclosure provided herein. In addition to the active ingredients, these pharmaceutical compositions may contain suitable pharmaceutically acceptable carriers comprising excipients and auxiliaries which facilitate processing of the active compounds into preparations which can be used pharmaceutically. Techniques for formulation and administration may be found in Remington's Pharmaceutical Sciences, 18th ed., Mack Publishing Co., Easton, Pa. (1990). Suitable routes may include oral, rectal, transdermal, vaginal, transmucosal, or intestinal administration; parenteral delivery, including intramuscular, subcutaneous, intramedullary injections, as well as intrathecal, direct intraventricular, intravenous, intraperitoneal, intranasal, or intraocular injections, just to name a few.

Preferred are pharmaceutical compositions for parenteral application. Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Optionally, the suspension may also contain suitable stabilizers or agents which increase the solubility of the compounds to allow for the preparation of highly concentrated solutions. Exemplary compositions for intramuscular, subcutaneous or intravenous application include isotonic aqueous solutions or suspensions, optionally prepared shortly before use from lyophilized or concentrated preparations. The pharmaceutical compositions may contain agents for conserving, stabilizing, wetting, emulsifying or solubilizing the ingredients, salts for the regulation of the osmotic pressure, buffer and/or compounds regulating the viscosity (e.g., sodium carboxycellulose, sorbitol, dextran, polyvinylpyrrolidine or gelatine). They are prepared by methods known in the art, e.g. by conventional mixing, dissolving or lyophilizing, and contain from about 0.01% to about 50% of active ingredients. The compositions for injections are processed, filled into ampoules or vials, and sealed under aseptic conditions according to methods known in the art.

The specific mode of administration and the dosage will be selected by the attending physician taking into account the particulars of the patient, the state of the disease, the type of melanoma treated, and the like. It should be noted that the attending physician would know how to and when to terminate, interrupt, or adjust administration due to toxicity, or to organ dysfunctions. Conversely, the attending physician would also know to adjust treatment to higher levels if the clinical response were not adequate (precluding toxicity). The magnitude of an administrated dose in the management of the disorder of interest will vary with the severity of the condition to be treated and to the route of administration. The severity of the condition may, for example, be evaluated, in part, by standard prognostic evaluation methods. Further, the dose and perhaps dose frequency, will also vary according to the age, body weight, and response of the individual patient. A program comparable to that discussed above may be used in veterinary medicine.

By "comprising" is meant including, but not limited to, whatever follows the word "comprising". Thus, use of the term "comprising" indicates that the listed elements are required or mandatory, but that other elements are optional and may or may not be present. By "consisting of" is meant including, and limited to, whatever follows the phrase "consisting of". Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

Other features and advantages of the invention will be apparent from the detailed description of the invention below and from the list of enumerated embodiments that follows.

IV. BRIEF DESCRIPTION OF THE DRAWINGS

FIG. 1A shows homogenous staining of compound nevus cells. The non-activated basal melanocytes are not stained.

FIG. 1B shows in-situ staining of melanoma.

FIG. 1C shows staining of superficial spreading melanoma (Clark level III, Breslow 0.91 mm).

FIG. 1D shows staining of melanoma lymph node metastasis.

SM5-1 stained the entire population of tumor cells in 1B-1D.

V. DETAILED DESCRIPTION OF THE INVENTION

A. Preparation of SM5-1 Antibody

SM5-1 antibody is selected from a panel of monoclonal antibodies generated by using a subtractive immunization protocol as previously described in Williams et al., (1992) *Biotechniques* 12:842–8477, and Brooks et al., (1993) *J. Cell Biol.* 22:1351–1359, both of which are incorporated by reference herein.

Briefly, mice were immunized with human melanoma cell line SMMU-1, which was obtained from the primary melanoma of a patient (Guo et al., (1994) *Cancer Res.* 54:561–1565, incorporated by reference herein). Next, the mice were treated with cyclophosphamide to abrogate activated B cells that produce antibody against epitopes expressed by the primary melanoma. The mice were then immunized with human melanoma cell line SMMU-2, which was obtained from the metastatic lesion of the same patient. The splenocytes from the mice were used for making hybridomas using standard techniques. Köhler G, Milstein C: Derivation of specific antibody producing tissue culture and tumor lines by cell fusion. *Eur. J. Immunol.* 1976; 6:511–519.

B. Immuno-histochemical Staining of Tissue Specimen

SM5-1 was determined by ELISA to be a mouse IgG1. SM5-1 was characterized for its reactivity with both frozen and paraffin embedded tissue samples. Supernatants from SM5-1 hybridoma were harvested and used for immuno-histochemical staining of tissues using the labeled streptavidin-biotin (LSAB) method (Large Volume LSAB kit, DAKO, Carpinteria, Calif., USA) as described elsewhere. Giorno R A: A comparison of two immunoperoxidase staining methods based on the avidin-biotin interaction. *Diag. Immunol.* 1984; 2:161–166.

Briefly, the specimens were incubated with the primary antibody followed by 10-minute incubations with biotinylated link antibody, peroxidase-labeled streptavidin and substrate chromogen-solution. For all experiments 1:50 diluted tissue culture supernatants of SM5-1 were used. Staining for SM5-1 was improved with pretreatment of tissue sections in a microwave oven and with trypsin. Shi S R, Key M E, Kalra K L: Antigen retrieval in formalin-fixed, paraffin-embedded tissues: an enhancement method for immuno-histochemical staining based on microwave oven heating of tissue sections. *J Histochem. Cytochem.* 1991; 39:741–748.

Samples of melanocytic lesions were also stained with HMB-45 (150, DAKO) and with a monoclonal antibody to S-100 protein (clone S 1/61/69, 1:20, Medac).

226 consecutive specimens of human melanoma were selected for staining, including 88 primary melanomas and 138 metastases (skin, lymph nodes). 16 nevi of various histological classifications (see Table 1) were selected for staining as non-melanoma melanocytic lesions specimens.

TABLE 1

Reactivity of SM5-1 with benign and malignant melanocytic lesions in comparison with HMB-45 and anti-S-100 on paraffin embedded sections

| Melanocytic lesions | Immunohistochemical staining with | | |
|---|---|---|---|
| | SM5-1 (positive/tested) | HMB-45 (positive/tested) | Anti-S-100 (positive/tested) |
| NEVI | | | |
| Compound | 6/6 | 6/6 | 6/6 |
| Dysplastic | 5/5 | 5/5 | 5/5 |
| Blue | 2/2 | 2/2 | 2/2 |
| Combined | 3/3 | 3/3 | 3/3 |
| Total | 16/16 (100%) | 16/16 (100%) | 16/16 (100%) |
| MELANOMA | | | |
| Primary melanoma | | | |
| MM in situ | 9/9 | 9/9 | 9/9 |
| Clark level II | 7/7 | 7/7 | 7/7 |
| Clark level III | 19/19 | 19/19 | 19/19 |
| Clark level IV | 47/47 | 46/47 | 47/47 |
| Clark level V | 6/6 | 6/6 | 6/6 |
| Total | 88/88 (100%) | 87/88 (98%) | 88/88 (100%) |
| Metastatic melanoma | 135/138 (100%) | 114/138 (83%) | 137/138 (100%) |
| Total for Melanoma | 223/226 (98%) | 201/226 (88%) | 225/226 (99%) |

The tissues were surgically removed, fixed in 10% buffered formaldehyde, embedded in paraffin, and processed for routine histology study.

Specimens of non-melanocytic tumors and benign tissues are listed in Table 2 and Table 3, some of which were provided by the Institute of Pathology, Charité, Germany.

TABLE 2

Reactivity of SM5-1 with non-melanocytic tumors on paraffin embedded sections.

| Tumor type | Immunohistochemical staining with SM5-1 |
|---|---|
| Skin | |
| Dermatofibrosarcoma protuberans | 0/2 |
| Merkel cell carcinoma | 0/1 |
| Sweat gland carcinoma | 0/3 |
| Sqnamous cell carcinoma | 0/4 |
| Brain | |
| Glioma | 0/1 |
| Astrocytoma | 0/4 |
| Oligodendroglioma | 0/1 |
| Meningeoma | 0/3 |
| Glioblastoma | 0/2 |
| Neurinoma | 0/1 |
| Gastrointestinal tract | |
| Esophageal carcinoma | 0/2 |
| Gastric carcinoma | 0/2 |
| Colon carcinoma | 0/2 |
| Pancreatic carcinoma | 0/2 |
| Others | |
| Bronchial carcinoma | 0/1 |
| Thyroid carcinoma | 0/1 |
| Breast carcinoma | 0/1 |
| Prostate carcinoma | 0/1 |
| Ovary carcinoma | 0/1 |
| Renal cell carcinoma | 0/1 |
| Leiomyosarcoma | 0/2 |
| M. Paget | 0/1 |
| Angioleiomyosarcoma | 0/1 |
| Angiosarcoma | 0/3 |
| Porocarcinoma | 0/1 |
| Urothel carcinoma | 0/1 |
| Osteosarcoma | 0/2 |
| Total | 0/46 |

C. SM5-1 Recognizes an Antigen in Malignant Melanoma and Nevi

Table 1 summarizes immuno-histochemical analyses of 226 melanomas and 16 nevi with SM5-1, HMB-45 and anti-S100.

Figure 1:
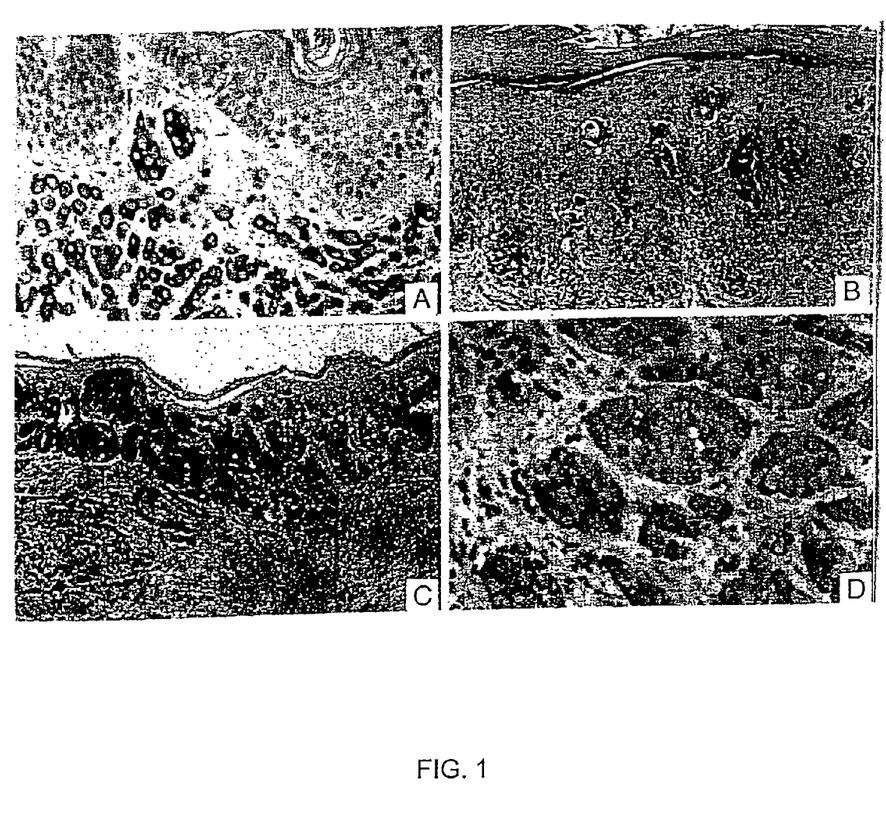
FIGS. 1A to 1D show immunohistochemical-staining of melanocytic lesions with monoclonal antibody SM5-1.

All of the tested primary melanoma and nevi were positive for SM5-1 irrespective of their histological type (superficial spreading, nodular, lentigo maligna, acral lentiginous) or Clark level. Generally, the staining was strong and involved the majority of the neoplastic cells. The pattern of the staining was both cytoplasmic and on the cell membrane. There was no difference in the strength or pattern of staining between primary lesions and metastatic lesions (FIG. 1).

HMB-45 was able to detect all of the examined primary melanoma and nevi. However, HMB-45 was only able to stain 83% (114/138) of metastatic melanoma. Most interestingly, all the HMB-45 negative melanomas were stained by SM5-1. In tissue samples stained by both SM5-1 and HMB-45, the epitopes for SM5-1 and for HMB-45 were found in different populations of the tumor. This indicates that the epitopes for SM5-1 and HMB-45 are different and, furthermore, they are expressed in different populations of melanoma tissue samples.

D. SM5-1 Reacted with Frozen Sections of Melanoma 36 melanoma specimens (17 primary melanomas, 19 metastases) obtained from surgical resection were split in half with one part being paraffin embedded and the other part snap frozen (snap frozen in liquid nitrogen and cut with a freezing microtome (5 μm)) and stained with SM5-1 (dilution 1:50) on cryostat sections. The cryostat sections were air-dried and fixed in acetone. All frozen sections reacted with SM5-1 in a pattern comparable with that seen in paraffin section.

E. SM5-1 Recognizes an Antigen in Human Hepatocellular Carcinoma Cell Lines

7 HCC cell lines established from human hepatocellular carcinoma tissue resected between August 1994 to December 1996 were tested by SM5-1. All of the HCC cells grow stably in RPMI-1640 medium supplemented with 10% FCS. Human B cells transfected with EBV were used as a negative control.

Hepatocellular cell lines were trypsinized to form single cell suspensions and washed with PBS, then 0.1 ml SM5-1 supernatant was added to $10^5$ tumor cells, incubated at 4° C. for 1 h, washed with PBS twice, then 0.1 ml FITC-GaM-IgG (FITC labeled Goat anti-mouse IgG (ZYMED, San Francisco), 1:50 in PBS) was added. After 40 minutes of incubation at 4° C., cells were washed with PBS twice. The samples were assayed at an FACSCaliber® cytometer. 6/7 of the hepatoma cell lines were stained positive by SM5-1.

An antigen was immuno-precipitated by SM5-1 antibody from the extracts of the HCC with the strongest staining signal as a protein of about 200 kilodalton (kD) apparent molecular weight as determined by sodium dodecyl sulfate gel electrophoresis.

F. SM5-1 Does Not Stain Non-melanocytic Malignant Tumors

In order to examine whether SM5-1 cross-reacts with malignancies other than melanomas, a large variety of paraffin embedded non-melanoma tumors (surgically removed) were examined for staining with SM5-1. These tissues included tumors from skin, brain, gastrointestinal tract and others. Table 2 shows that none of the 27 non-melanocytic tumors reacted with SM5-1.

G. SM5-1 Does Not Stain Most Normal Human Tissues

Table 3 summarizes staining data with nonmalignant human tissues. Most normal cells were not stained with SM5-1 except for weak staining with plasma cells, the secretion of eccrine sweat gland, the secretory epithelium of thyroid, some myofibroblasts, and perivascular dendritic cells. This limited pattern of unspecific staining is comparable to the unspecific staining by HMB-45. Colombari R, Bonetti F, Zamboni G, Scarpa A, Marino F, Tomezzoli A et al: Distribution of melanoma specific antibody (HMB-45) in benign and malignant melanocytic tumors. *Virchows Archiv. A Pathol. Anat.* 1988; 413:17–24.

TABLE 3

Reactivity of SM5-1 with normal tissues, normal cells and benign lesions

| Tissue or lesion | immunohistochemical staining with SM5-1 |
|---|---|
| | NEGATIVE |
| Glomerulus | --- |
| Ciliated epithelium | --- |
| Beaker cells | --- |
| Sebacious glands | --- |
| Liver tissue | --- |
| Normal melanocytes | --- |
| Keratinocytes | --- |
| Langerhans cells | --- |
| Peripheral nerves | --- |
| Neutrophilic granulocytes | --- |

TABLE 3-continued

Reactivity of SM5-1 with normal tissues, normal cells and benign lesions

| Tissue or lesion | immunohistochemical staining with SM5-1 |
|---|---|
| Smooth muscle cells | --- |
| Gastric mucosa | --- |
| Ependymoma | --- |
| Keloid | --- |
| Activated melanocytes | --- |
| | WEAKLY POSITIVE |
| Activated macrophages | + |
| Myofibroblasts | + |
| Plasma cells | + |
| Secretion of eccrine sweat glands | + |
| Secretory epithelium of thyroid | + |

H. Staining Pattern of SM5-1

With regard to the staining pattern we found that HMB-45 staining is cytoplasmic and granular whereas for SM5-1 it is more homogenous and both cytoplasmic and on the cell membrane. This suggests that the two antibodies recognize different antigens.

The results show that SM5-1 is more sensitive than HMB-45 and more specific than anti-S-100 antibodies in detecting melanoma lesions.

I. Utility of SM5-1

Melanoma patients have a significantly increased risk of developing a second primary tumor, e.g. lung cancer. Swerdlow A J, Storm H H, Sasieni P D: Risks of second primary malignancy in patients with cutaneous and ocular melanoma in Denmark, 1943–1989. *Int. J. Cancer* 1995; 61:773–779. Therefore, it is of great importance to analyze and identify any lesion or suspected parenchymal lesion in melanoma patients, e.g., by fine needle aspiration. The ability of SM5-1 to reliably recognize metastases of malignant melanoma in patients bearing poorly differentiated tumors is very useful in such procedures. In one series of cases a second pulmonary neoplasia could be identified in three of 50 melanoma patients by using two different antibodies for the immunocytochemical diagnosis. Mottolese M, Venturo I, Benevolo M, Di-Filippo F, Lopez M, Bigotti A et al: Immunocytochemical diagnosis of amelanotic metastatic melanoma using monoclonal antibodies HMB-45 and Ep 1-3. *Melanoma Res.* 1994; 4:53–58. Using SM5-1 can render it unnecessary to use a panel of antibodies in such cases.

By using SM5-1 one can correctly diagnose a lesion as being of melanocytic origin. The differentiation between a nevus and a melanoma can usually then be done with relative ease by histological criteria. SM5-1 can be used in routinely processed paraffin embedded or cryostat melanoma sections.

All publications cited in the specification are incorporated by reference herein, including drawings and sequences listed in each publication. All the compounds disclosed and referred to in the publications mentioned above are incorporated by reference herein, including those compounds disclosed and referred to in articles cited by the publications mentioned above.

Other embodiments of this invention are disclosed in the following claims.

What is claimed is:

1. A method for detecting melanoma cells in a human host, comprising the steps of:
   combining a sample of bodily fluid from the human host with a monoclonal antibody which binds specifically to an antigen, and detecting cells or cell membranes which bind to the monoclonal antibody as indicative of melanoma cells in the host, wherein,
(a) said antigen is specifically bound by the antibody produced by the hybridoma deposited under ATCC Acession No. HB-12588,
(b) said antigen is present on the membrane and in the cytoplasm of human melanoma cells,
(c) said antigen is not present in normal, non-activated human melanocytic cells and non-melanocytic cells in an amount that is detectable by the antibody produced by the hybridoma deposited under ATCC Acession No. HB-12588, and
(d) said monoclonal antibody competitively inhibits specific binding of the antibody produced by the hybridoma deposited under ATCC Acession No. HB-12588 to the antigen.

2. The method according to claim 1, wherein said bodily fluid is blood.

3. The method according to claim 2, wherein said monoclonal antibody is a humanized monoclonal antibody.

4. A method for detecting melanoma cells in a human host, comprising the steps of:
combining a sample of bodily fluid from the human host with a monoclonal antibody which binds specifically to an antigen, and
detecting cells or cell membranes which bind to the monoclonal antibody as indicative of melanoma cells in the host, wherein the detecting of the cells which bind to the monoclonal antibody is carried out by detecting a label present on said monoclonal antibody, or detecting a label present on a secondary antibody, wherein said label is technetium 99, a fluorescer, a radioopaque dye, or an enzyme, and wherein
(a) said antigen is specifically bound by the antibody produced by the hybridoma deposited under ATCC Accession No. HB-12588,
(b) said antigen is present on the membrane and in the cytoplasm of human melanoma cells,
(c) said antigen is not present in normal, non-activated human melanocytic cells and non-melanocytic cells in an amount that is detectable by the antibody produced by the hybridoma deposited under ATCC Accession No. HB-12588, and
(d) said monoclonal antibody competitively inhibits specific binding of the antibody produced by the hybridoma deposited under ATCC Accession No. HB-12588 to the antigen.

5. A method for detecting melanoma cells in a human host, comprising the steps of:
combining a sample of blood from the human host with a monoclonal antibody which binds specifically to an antigen, and
detecting formation of immune complexes formed by the specific binding of the monoclonal antibody to the antigen as indicative of the presence of melanoma cells in the host, wherein the detection of immune complexes is carried out by detecting a label present on said monoclonal antibody, or detecting a label present on a secondary antibody, wherein said label is technetium 99, a fluorescer, a radioopaque dye, or an enzyme, and wherein
(a) said antigen is specifically bound by the antibody produced by the hybridoma deposited under ATCC Accession No. HB-12588,
(b) said antigen is present on the membrane and in the cytoplasm of human melanoma cells,
(c) said antigen is not present in normal, non-activated human melanocytic cells and non-melanocytic cells in an amount that is detectable by the antibody produced by the hybridoma deposited under ATCC Accession No. HB-12588, and
(d) said monoclonal antibody competitively inhibits specific binding of the antibody produced by the hybridoma deposited under ATCC Accession No. HB-12588 to the antigen.

\* \* \* \* \*

UNITED STATES PATENT AND TRADEMARK OFFICE
CERTIFICATE OF CORRECTION

PATENT NO. : 7,666,609 B1  Page 1 of 1
APPLICATION NO. : 09/915746
DATED : February 23, 2010
INVENTOR(S) : Yajun Guo et al.

It is certified that error appears in the above-identified patent and that said Letters Patent is hereby corrected as shown below:

Title page, item (*) Notice: Subject to any disclaimer, the term of this patent is extended or adjusted under 35 U.S.C. 154(b) by 161 days.

Delete the phrase "by 161 days" and insert --by 803 days--;

Title Page, References Cited, Other Publications, Aamdal et al. reference, please delete "Immunomagnetie" and insert --Immunomagnetic-- therefor;

Title Page, References Cited, Other Publications, Adema et al. reference, please delete "Chem:" and insert --Chem.-- therefor;

Title Page, References Cited, Other Publications, Argenyi et al. reference, please delete "Demiatopathol." and insert --Dermatopathol.-- therefor;

Title Page, References Cited, Other Publications, Cohen et al. reference, please delete "Mcinoclonal" and insert --Monoclonal-- therefor;

Title Page, References Cited, Other Publications, Drier et al. reference, please delete "S100." and insert --S100-- therefor;

Column 17, line 12 (Claim 1), please delete "Acession" and insert --Accession-- therefor;

Column 17, line 16 (Claim 1), please delete "Acession" and insert --Accession-- therefor;

Column 17, line 33 (Claim 4), please delete "radioopaque" and insert --radiopaque-- therefor;

Column 18, line 22 (Claim 5), please delete "radioopaque" and insert --radiopaque-- therefor.

Signed and Sealed this

Fourteenth Day of September, 2010

David J. Kappos
*Director of the United States Patent and Trademark Office*